United States Patent
Liu et al.

(10) Patent No.: US 6,746,484 B1
(45) Date of Patent: Jun. 8, 2004

(54) SPINAL IMPLANT

(75) Inventors: Mingyan Liu, Bourg-la-Reine (FR); Philippe Bouquet, Lamorlaye (FR); Hans-Jorg Meisel, Berlin (DE); Daniel Chopin, Grofflieres (FR)

(73) Assignee: Society de Fabrication de Materiel de Orthopedique, S.A. (FR)

( * ) Notice: Subject to any disclaimer, the term of this patent is extended or adjusted under 35 U.S.C. 154(b) by 0 days.

(21) Appl. No.: 09/486,301

(22) PCT Filed: Aug. 25, 1998

(86) PCT No.: PCT/IB98/01324

§ 371 (c)(1),
(2), (4) Date: Oct. 6, 2000

(87) PCT Pub. No.: WO99/09913

PCT Pub. Date: Mar. 4, 1999

(30) Foreign Application Priority Data

Aug. 26, 1997 (FR) .......................................... 97 10664

(51) Int. Cl.[7] .................................................. A61F 2/44
(52) U.S. Cl. ................................. 623/17.16; 623/17.11
(58) Field of Search ......................... 623/17.11, 17.16; 606/178, 184

(56) References Cited

U.S. PATENT DOCUMENTS

| 4,936,848 A | 6/1990 | Bagby ........................ 623/17 |
| 5,015,247 A | 5/1991 | Michelson .................... 606/61 |
| 5,062,845 A | 11/1991 | Kuslich et al. ................ 606/80 |
| 5,190,548 A | 3/1993 | Davis ......................... 606/80 |
| 5,250,061 A | 10/1993 | Michelson .................. 606/160 |
| 5,304,191 A | 4/1994 | Gosselin ..................... 606/172 |
| 5,306,309 A | 4/1994 | Wagner et al. ................ 623/17 |
| 5,425,772 A | 6/1995 | Brantigan ................. 623/17.11 |
| 5,443,514 A | 8/1995 | Steffee ........................ 623/17 |
| 5,445,639 A | 8/1995 | Kuslich et al. ................ 606/80 |
| 5,458,638 A | 10/1995 | Kuslich et al. ............... 623/17 |
| 5,484,437 A | 1/1996 | Michelson .................... 606/61 |
| 5,499,984 A | 3/1996 | Steiner et al. ................. 606/80 |
| 5,607,424 A | 3/1997 | Tropiano ..................... 606/61 |
| 5,609,635 A | 3/1997 | Michelson ................... 623/17 |
| 5,609,636 A | 3/1997 | Kohrs et al. .................. 623/17 |
| 5,649,945 A * | 7/1997 | Ray et al. .................... 606/167 |

(List continued on next page.)

FOREIGN PATENT DOCUMENTS

| DE | 3630863 A1 | 3/1988 |
| EP | 0195455 A1 | 3/1986 |
| EP | 0276153 A2 | 7/1988 |
| EP | 0493698 B1 | 7/1992 |
| EP | 0637440 A1 | 2/1995 |
| EP | 0646366 A1 | 4/1995 |
| EP | 0834295 A1 | 4/1998 |
| FR | 2724312 | 3/1996 |
| FR | 2727004 | 5/1996 |
| FR | 2736538 | 1/1997 |
| WO | WO94/10927 | 5/1994 |
| WO | WO95/08306 | 3/1995 |
| WO | WO96/27348 | 9/1996 |
| WO | WO97/23174 | 3/1997 |

Primary Examiner—Paul B. Prebilic
(74) Attorney, Agent, or Firm—Woodard, Emhardt, Moriarty, McNett & Henry LLP

(57) ABSTRACT

A spinal cage implant (1) is adapted to be inserted in a damaged intervertebral disc for restoring the discal height and permitting an arthoesis. Implant (1) comprises a central part (3c) with walls (4) and terminal parts (5, 6) for bearing against the cortical bone (14) of the vertebral end plates (15, 16). Central part (3c) is adapted to penetrate the vertebral end plates (15, 16) and transversely projects from the terminal bearing parts (5, 6). Implant (1) bears against the vertebral end plates (15, 16) with terminal parts (5, 6) and contains bone graft material between walls (4) which penetrate the openings (19, 21) in the end plates (15, 16) and permit bone fusion between the two vertebrae (V1, V2). Implant (1) permits restoring the physiological lordosis and the intervertebral height

18 Claims, 4 Drawing Sheets

U.S. PATENT DOCUMENTS

| | | | |
|---|---|---|---|
| 5,669,909 A | 9/1997 | Zdeblick et al. | 606/61 |
| 5,683,463 A | 11/1997 | Godefroy et al. | 623/17 |
| 5,720,749 A | 2/1998 | Rupp | 606/79 |
| 5,766,252 A | 6/1998 | Henry et al. | 623/17 |
| 5,782,830 A | 7/1998 | Farris | 606/61 |
| 5,846,244 A * | 12/1998 | Cripe | 606/82 |
| 5,857,995 A | 1/1999 | Thomas et al. | 604/22 |
| 5,888,224 A | 3/1999 | Beckers et al. | 606/60 |
| 5,888,227 A | 3/1999 | Cottle | 623/17 |
| 5,893,890 A | 4/1999 | Pisharodi | 623/17 |
| 6,080,158 A | 6/2000 | Lin | 606/61 |

* cited by examiner

SPINAL IMPLANT

TECHNICAL FIELD

The present invention relates to spinal implant devices and associated techniques for promoting fusion of two or more vertebrae.

BACKGROUND

It is known that when an intervertebral disc degenerates or is damaged, there is often a compression of the disc and a reduction in the normal intervertebral height. Typically, this condition results in abnormal motions that become a source of pain.

In order to treat a pathology of this type, the disc is often stabilized to eliminate the abnormal motions caused by disc disorders or injuries. Generally, one approach is to prevent articulation between the two vertebrae situated on each side of the damaged disc by bone fusion. This fusion fixes the vertebrae to each other, eliminating the relative mobility causing the pain.

Various spinal implants to promote fusion between adjacent vertebrae have been proposed. It has been proposed to interconnect the two vertebrae by a kind of rigid U-shaped stirrup which restores the discal height with a bone graft material disposed inside the stirrup. However, one drawback of this proposal is its diminishing effectiveness over a period of time.

An spinal cage is also known which consists of a cylindrical member provided with a series of openings and provided with anchoring points. This implant is placed in a recess formed in the intervertebral disc and penetrates the opposite cortical plates of the two vertebrae which were previously hollowed out to receive the implant. This penetration forms openings in the sub-chondral plates to place spongy bone of the vertebrae in contact with bone graft material placed inside the implant, facilitating bone fusion. U.S. Pat. No. 5,015,247 provides one example of this approach.

FR 2,736,538 discloses an intersomatic cage formed by a body having inclined upper and lower surfaces and parallel lateral walls, provided at their end portions with anti-backward movement teeth. In such a structure the central and end surfaces are in the same plane so that the major part of the bearing surface is provided by the central part, that is in contact with the spongy bone, of which the strength is lower than the strength of cortical plates. Hence such structure is not entirely satisfying.

Proper performance of a spinal implant of this type requires balancing the need to promote fusion between the spongy bone and the need to form a reliable load bearing relationship with the stronger cortical bone. As a result, the spinal cage must be neither engaged too far into the openings provided in the cortical plates to provide a sufficiently dense load bearing surface, nor insufficiently inserted, in which case the bone fusion between the two vertebrae would be adversely affected by a poor anchorage. Thus, there is a demand for devices and techniques that facilitate attaining the proper balance between fusion and load support.

The present invention meets this demand and provides other significant benefits and advantages.

DISCLOSURE OF THE INVENTION

The present invention relates to spinal fusion implants and techniques. Various aspects of the present invention are novel, nonobvious, and provide various advantages. While the actual nature of the invention covered herein can only be determined with reference to the claims appended hereto, certain forms which are characteristic of the preferred embodiments disclosed herein are described briefly as follows.

According to one form of the invention, the spinal implant comprises a body having a central part arranged to allow arthrodesis and at least one terminal part for bearing against the cortical bone of the vertebral end plates. The central part is adapted to penetrate the vertebral end plates, transversely projecting from the terminal bearing part. Thus the invention achieves a separation between the end parts constituting the load bearers, and the intermediate part of the implant which permits fusion. In addition, the central part may include at least one cavity for receiving a bone graft material.

In another form of the present invention, an implant for insertion between a first vertebra having a first cortical bone plate and a second vertebra having a second cortical bone plate includes two terminal parts. The first terminal part defines a first bearing surface to bear against the first cortical bone plate and a second bearing surface opposite the first surface to bear against the second cortical bone plate. The second terminal part opposes the first terminal part and defines a third bearing surface to bear against the first cortical bone plate and a fourth bearing surface opposite the third surface to bear against the second cortical bone plate. The implant has an elongated central part defining an upper projection extending past the first and third surfaces, and a lower projection extending past the second and fourth surfaces. These projections correspondingly pass through openings in the first and second cortical bone plates when the first and third surfaces bear against the first cortical bone plate and the second and fourth surfaces bear against the second cortical bone plate. The terminal parts are dimensioned to facilitate restoration of the natural geometry of the intervertebral space (lordosis, cyphosis, and parallel discs). Thus, the first and second surfaces may be separated by a first distance, and the third and fourth surface may be separated by a second distance greater than the first distance to accommodate a natural curvature of the spine.

In a further form of the present invention, an implant with two terminal parts also has an elongated central part that includes a pair of longitudinal walls defining a cavity. The walls define a first edge projecting past the first and third surfaces and a second edge projecting past the second and fourth surfaces. The first and second edges correspondingly penetrate the first and second cortical bone plates when the first and third surfaces bear against the first cortical bone plate and the second and fourth surfaces bear against the second cortical bone plate.

According to another form, the bearing surfaces of the terminal end parts are defined by flanges extending from opposing ends of the implant along its longitudinal axis. Preferably, the bearing surfaces are generally flat for bearing against the cortical bone of the vertebral end plates of the two adjacent vertebrae. It is also preferred that openings be cut into the cortical plates in their central regions corresponding to the length of a central part of the implant along the longitudinal axis and leaving a region of the cortical bone plates around the periphery of the openings. The length of the remaining peripheral plate corresponds to the length of the bearing surfaces along the longitudinal axis. When the implant is placed in position, the edges of the walls of the central part engage the openings cut in the cortical plates and consequently do not substantially bear against the remaining peripheral portion of the plates. A cavity may be defined by the central part that holds bone graft material in contact with the spongy bone of the two vertebrae. In contrast, the bearing surfaces of the flanges are disposed adjacent the edges of the openings of the cortical plates and bear against the remaining portions of the plates to establish a strong load bearing relationship. Thus, both bone fusion and support are distinctly accommodated by different parts of the implant structure, which permits obtaining a satisfactory support of the vertebral bodies on the implant and an excellent arthrodesis.

Yet another form of the present invention includes a cutting tool accessory to prepare the cortical plates of two adjacent vertebrae for insertion of an implant. This tool comprises a proximal handle connected to an elongate shaft configured to rotate about a longitudinal axis of the tool. The tool also includes a first non-cutting portion with the shaft extending therethrough and being configured to rotate relative thereto. A cutting portion is fixed to the shaft to rotate therewith and is positioned distal to the first non-cutting portion. The cutting portion includes a first pair of generally parallel opposing faces and a second pair of opposing faces each extending between the first pair of faces. The second pair of faces each define a number of cutting teeth. A second non-cutting portion is fixed to the cutting portion that includes a distal head. The first non-cutting portion, the cutting portion, and the second non-cutting portion have a rotatably selectable alignment that presents a generally constant height corresponding to the intersomatic space defined between the cortical bone plates to facilitate insertion therein. Once inserted, the cutting portion may be rotated out of this alignment to cut a first opening in the first cortical bone plate and a second opening into the second cortical bone plate. The cutting portion and to non-cutting portions may be arranged to provide uniform, symmetrical cutting of these openings with a predetermined length corresponding to the dimensions of a given implant device.

In an additional form, a technique of spinal fixation includes cutting adjacent vertebrae and inserting an implant therebetween to promote fusion and provide suitable support. The implant may be inserted by anterior or posterior surgical approaches. The cutting may be performed by the cutting tool of the present invention and may include initially inserting the tool so that a first pair of faces are in contact with a respective one of the first and second cortical bone plates, turning a handle to rotate the cutting portion to remove cortical bone with cutting teeth defined by a second pair of faces, and withdrawing the tool. The tool may be used to form openings readily positioned in the central region of the adjacent vertebrae that leaves cortical bone plate about the openings. The insertion of the implant may include positioning the implant of the present invention between the first and second vertebrae and turning the implant about one quarter of a turn.

It is envisioned that the implants of the present invention may be used with other tools and procedures, that the tools of the present invention may be used with other implants and procedures, and that the procedures of the present invention may be used with other implants and tools as would occur to those skilled in the art without departing from the spirit of the present invention.

Accordingly, one object of the invention is to provide a spinal implant arranged to facilitate proper fusion of two or more vertebrae. The implant may be arranged to have at least one structural part to promote bone fusion through contact with spongy vertebral bone and one or more other structural parts adapted for contact with cortical bone to provide load support.

Another object is to provide a tool accessory to facilitate implantation of devices suitable to promote fusion.

Still another object is to provide a technique for preparing a site between two vertebrae to be fused and inserting an implant.

Other objects, features, benefits, forms, aspects, and advantages of the present invention will become apparent from the description and drawings herein.

MODE(S) FOR CARRYING OUT THE INVENTION

Figure 1:
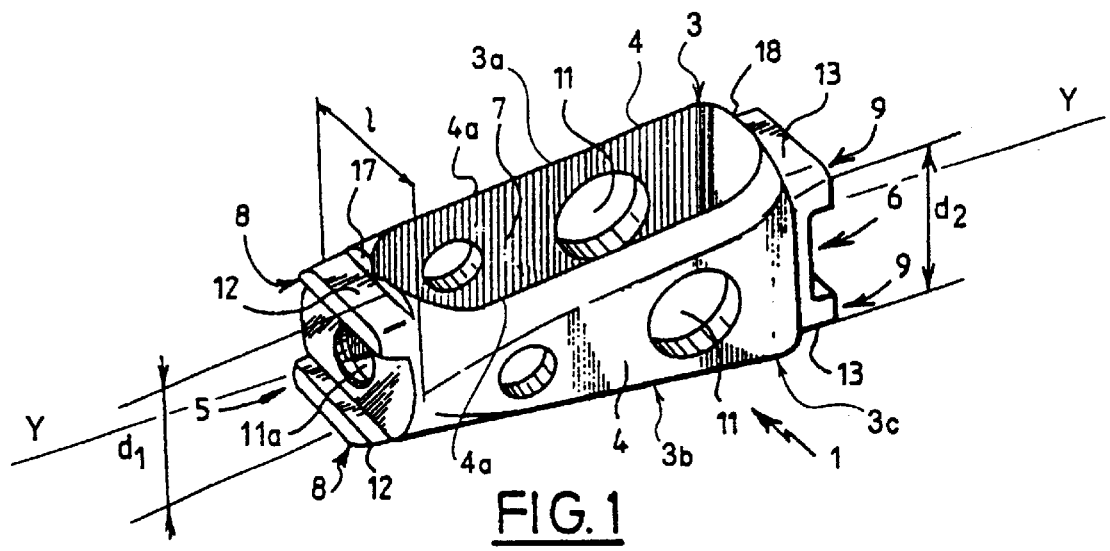
FIG. 1 is a perspective view, to a larger scale, of one embodiment of a spinal implant of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

Figure 6:
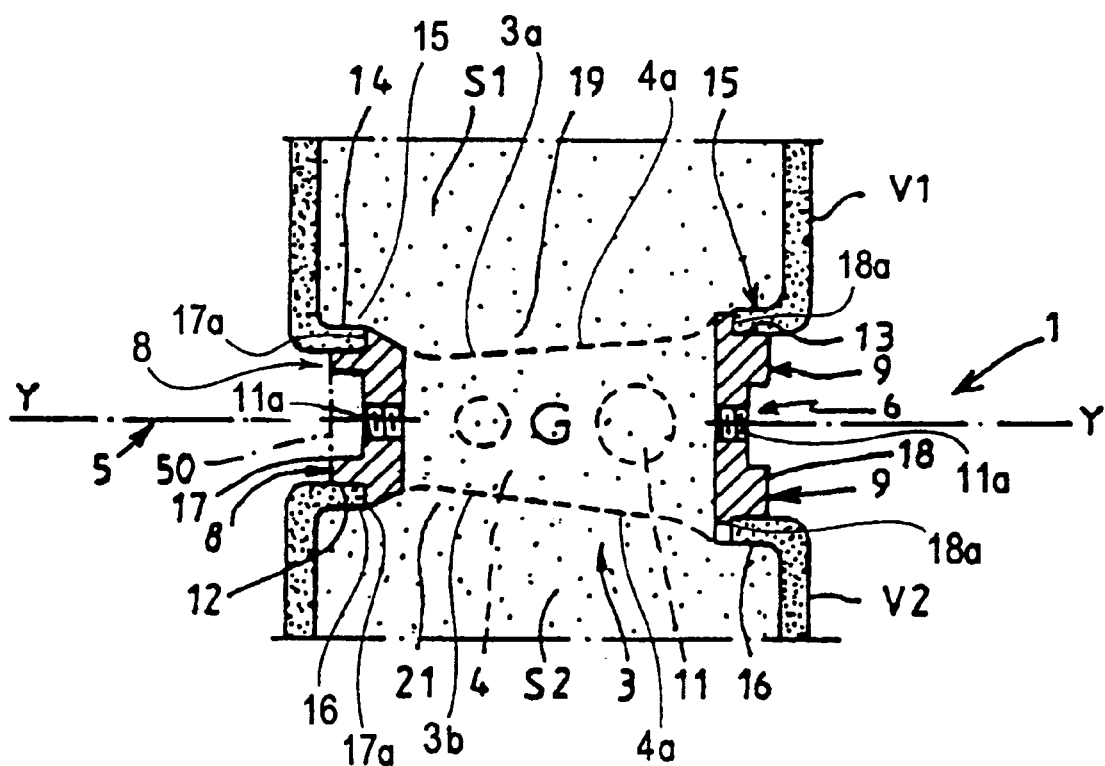
FIG. 6 is a partial sectional view taken in a sagittal plane showing the implant of FIG. 1 positioned in an intervertebral disc for achieving a spinal fusion.
Figure 7:
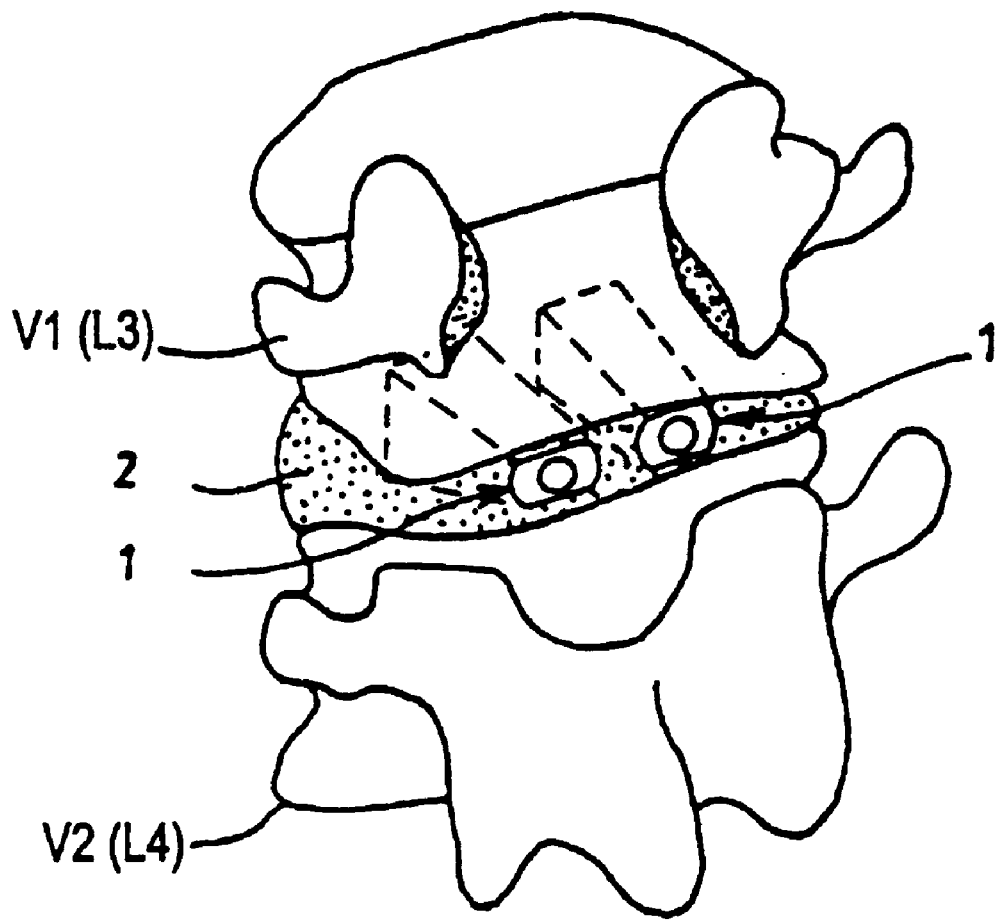
FIG. 7 is a perspective view of a spinal segment in the intervertebral disc in which two implants have been installed.

FIGS. 1, 6, and 7 depict spinal cage implant 1. Implant 1 is adapted to be inserted in a cavity provided in a damaged intervertebral disc 2 (FIG. 7), so as to restore the normal height of the intervertebral space between the two vertebrae V1 and V2 adjacent to the disc 2, for example the lumbar vertebrae L3, L4 as depicted in FIG. 7. FIG. 1 shows implant 1 disposed along its longitudinal axis YY. Implant 1 comprises a hollow body 3 of elongate shape, having a central part 3c formed by two parallel longitudinal walls 4 arranged to permit the arthrodesis and, at the two opposite ends of the central part 3c, in the direction of the implantation of the implant 1, two terminal parts 5, 6 for bearing against the cortical bone 14 of vertebral cortical bone plates 15, 16 of the two vertebrae (V1, V2) adjacent to the disc 2 (see, for example, FIG. 6).

The longitudinal walls 4 define therebetween a cavity 7 and are provided with openings 11. Terminal parts 5, 6 are disposed opposite each other along axis YY and each include a terminal face defining a centrally located threaded hole 11a. Holes 11a are configured for engagement by a threaded shaft of an insertion/manipulation accessory (no shown) to facilitate placement of implant 1 between vertebrae V1, V2. The cavity 7 is provided to receive a graft G of spongy bone or any other material favoring bone fusion, for example a synthetic ceramic.

Terminal part 5 has two opposite bearing surfaces 12 transverse to axis YY which are so dimensioned that they are separated by distance d1. Terminal part 6 has two opposite bearing surfaces 13 transverse to axis YY which are so dimensioned that they are separated by distance d2. Distances d1, d2 are adapted to the geometry of the intervertebral space to be restored. When d2 is greater than d1 as depicted, implant 1 is preferred for fusion of vertebrae in a region of the spine having a natural curvature. Distance 1 corresponds to a maximum width dimension of body 3. In one embodiment, the width of body 3 is generally constant along axis YY and is about the same as distance d1 to facilitate a proper fit between vertebrae V1, V2 as will become more apparent hereinafter.

The terminal parts 5, 6 are extended by load bearing flanges 8, 9, namely two load bearing flanges 8 for part 5 and two load bearing flanges 9 for part 6. In the depicted embodiment, flanges 8, 9 form parallel bars perpendicular to the longitudinal walls 4, and define generally flat surfaces 12, 13 for bearing against the cortical bone 14 of the vertebral end plates 15, 16.

In the illustrated embodiment, the longitudinal walls 4 have a substantially trapezoidal contour of which the small base corresponds to the terminal part 5 and the large base corresponds to the terminal part 6. The walls 4 constituting the central part 3c of the implant 1 are so shaped as to transversely project from the terminal bearing parts 5, 6, as can be seen in FIGS. 1 and 6. Thus the walls 4 can penetrate respective openings 19, 21 of the vertebral plates 15, 16 whose edges bear against the bearing surfaces 12, 13 of the flanges 8, 9 (FIG. 6). Flanges 8, 9 are shaped to define step projections 17a, 18a to further facilitate penetration of openings 19, 21. Projections 17a, 18a also provide a lip to maintain alignment of bearing surfaces 12, 13 with cortical bone plates 15, 16 about the periphery of the openings as shown in FIG. 6. Walls 4 also include tapered edges 4a to facilitate penetration. Correspondingly, central part 3c has upper projection 3a and lower projection 3b defined by edges 4a. Notably, edges 4a and projections 3a, 3b transversely project away from surfaces 12, 13.

Figure 2:
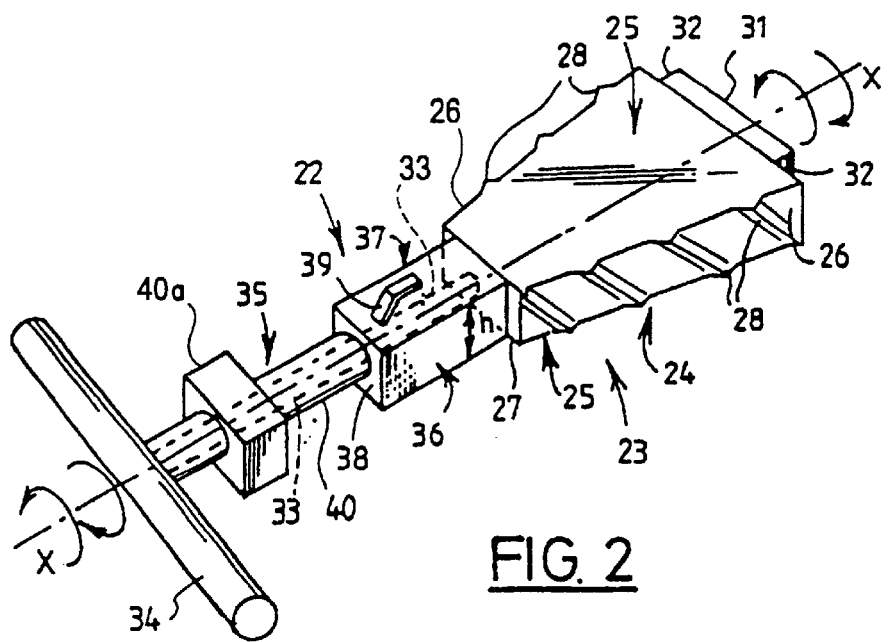
FIG. 2 is a perspective view of one embodiment of a cutting tool of the present invention for mounting the implant of FIG. 1.

Implant 1 may be placed in position in the intervertebral disc 2 after preparation with cutting tool accessory 22 which will now be described with reference to FIGS. 2, 4, and 5. Preferably, tool 22 is made from a metallic material suitable for surgical use. Tool 22 has a milling cutter 23 including central cutting portion 24 and two non-cutting portions 31, 36 arranged at opposite ends of central cutting portion 24. Non-cutting portions 31, 36 have height h corresponding to the intersomatic space and permitting uniform, symmetrical cutting of a predetermined length through a central region of both vertebral plates 15, 16. Preferably, the geometry of portions 24, 31, 36 is determined for preparing the intersomatic space with the geometry of implant 1 to restore the natural lordosis of the intervertebral space, and correspondingly the distances represented by h and d1 are approximately equal.

Central cutting portion 24 has a trapezoidal shape with two generally smooth, longitudinal faces 25 opposed to each other. Faces 25 are configured to facilitate insertion into the intersomatic space being generally separated from each other by distance h. Central cutting portion 24 also has cutting faces 26 extending between faces 25. Cutting faces 26 define a number of uniformly spaced apart cutting teeth 28. Teeth 28 each extend along a generally straight path that is slanted at an oblique angle relative to longitudinal axis XX of tool 22. Preferably, central cutting portion 24 is made from a suitable metallic material that has been machined to form teeth 28.

Non-cutting portion 31 is fixed to the distal end of central cutting portion 24. Portion 31 extends from central cutting portion 24 to provide a distal head in the form of a parallelepiped-shaped bar. Portion 31 has a first dimension substantially the same as distance h to be generally coextensive with faces 25 of central cutting portion 24. Portion 31 also has opposing faces 32 separated from each other by a distance H as shown in FIG. 5. Preferably distance H is approximately equal to distance d2 when tool 22 is being utilized to install implant 1.

Tool 22 also includes a shaft or shank 33 connected to a proximal actuating handle 34. Shank 33 is fixed to central cutting portion 24 and non-cutting portion 31. Shank 33 extends from the small end face 27 remote from the non-cutting head 31 and terminates in the handle 34 which permits rotating the cutting portion 24 about the longitudinal axis XX of tool 22.

Non-cutting portion 36 has a rectangular shape with generally planar faces 37, 38. Portion 36 may be inserted between two consecutive vertebrae during rotation of central cutting portion 24. Portion 36 extends in the direction toward the handle 34 by a tubular part 40 and through block 40a which terminates in the vicinity of the handle 34. Non-cutting portion 36 is provided with lateral stops 39 capable of being put into abutment against the sides of the vertebrae (V1, V2) after insertion therebetween. Non-cutting portion 36 encloses shank 33. Shank 33 is configured to rotate relative to portion 36. Correspondingly, when handle 34 is turned, shank 33, central cutting portion 24, and non-cutting portion 31 rotate together about axis XX with non-cutting portion 36 preferably remaining stationary. It should be noted that the partial view of FIGS. 4 and 5 do not show handle 34 and depict a cutaway view of non-cutting portion 36 with shank 33 projecting therefrom.

Various nonlimiting embodiments of a spinal fixation or fusion procedure of the present invention are next described. One procedure is characterized by: (a) cutting the vertebrae V1, V2 and disc 2 with tool 22 to prepare for implantation and (b) inserting the implant 1 between vertebrae V1, V2. Another more detailed procedure for fusing two vertebrae together is described in terms of procedural stages (a)–(h) as follows:

(a) A surgeon first separates the dural sleeve forming the extension of the bone marrow if the procedure is in the lumbar region and then carries out a discectomy to provide space for implant 1 in disc 2.

Figure 3:
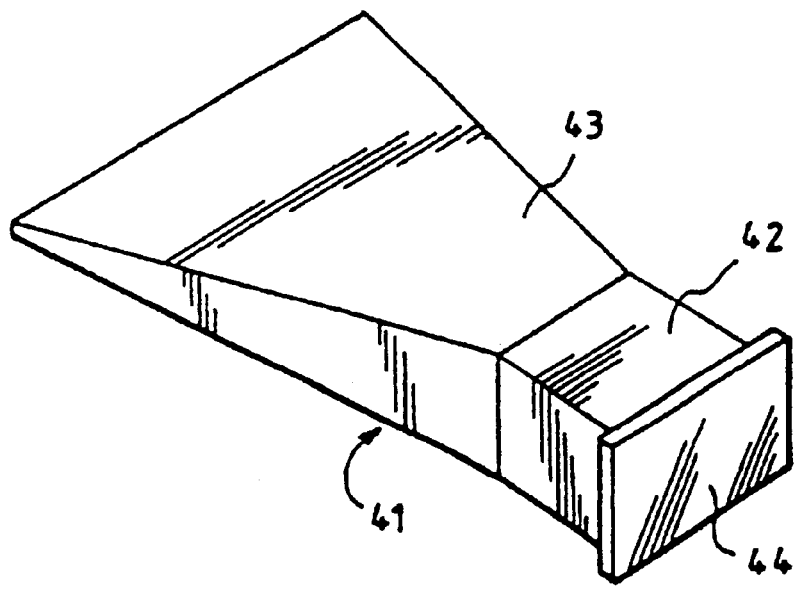
FIG. 3 is a perspective view of a distracting wedge or "distractor" used for carrying out a surgical method in accordance with the present invention.

(b) The surgeon inserts between the two vertebrae V1, V2 from the rear (posterior), two lordosis distractors 41 as shown in FIG. 3. Each distractor 41 consists of a parallelepiped-shaped part 42 extended by a wedge part 43 of triangular section. Part 42 is provided with thrust plate 44. Distractors 42 are inserted laterally with respect to the cavity provided by the discectomy of stage (a). Each distractor 41 is initially inserted by presenting its narrower aspect between V1 and V2, and, then turned through 90° so as to spread apart the vertebrae and restore the discal height and the height of the considered vertebral segment. Next, one of the distractors 41 is removed.

Figure 4:
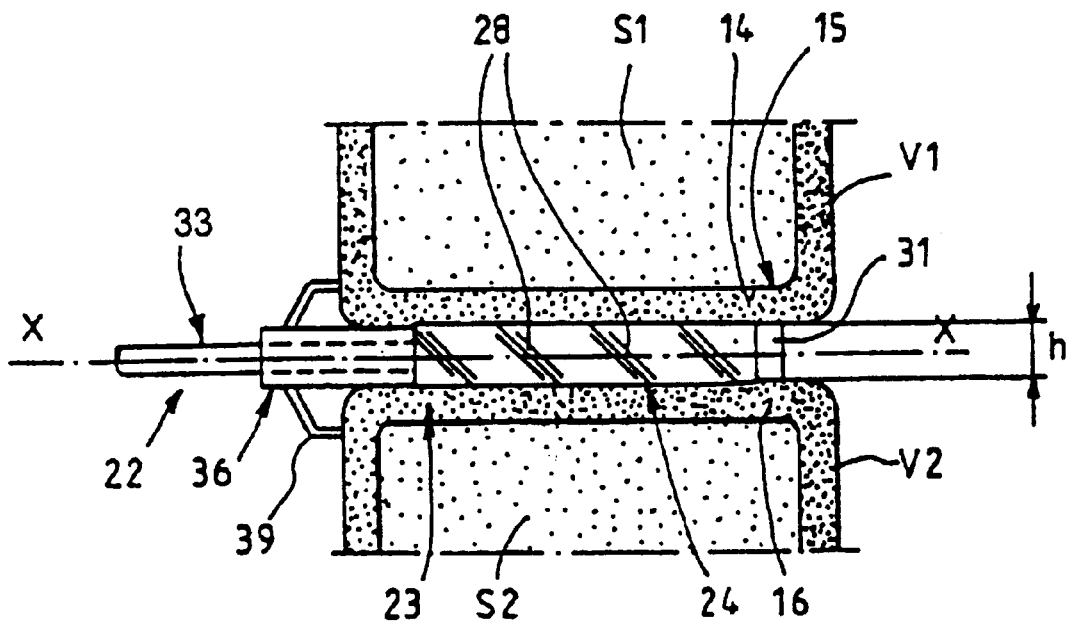
FIG. 4 is a partial elevational view diagrammatically illustrating the insertion of the cutting tool between two vertebrae.
Figure 5:
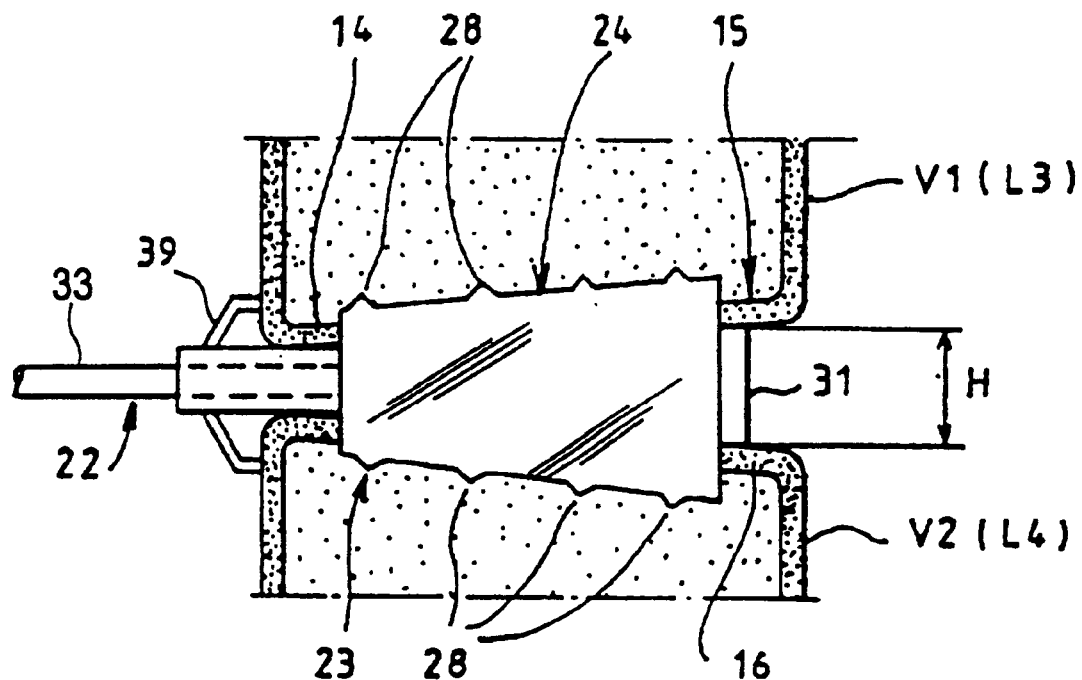
FIG. 5 is a partial elevation view showing the cutting tool after rotation of the cutting portion through 90° and penetrating the cortical plates of the two adjacent vertebrae.

(c) The surgeon inserts tool 22 between the vertebrae V1, V2 as shown in FIG. 4 so that the larger, smooth faces 25 are in contact with the vertebral plates 15, 16. When the cutting portion 24 is correctly positioned in the central region of the cortical plates, stops 39 come into abutment with the outer surface of the vertebrae V1, V2 and non-cutting portion 36 is partly inserted between the plates 15, 16.

(d) Next, the surgeon turns handle 34, causing cutting portion 24 to rotate about axis XX. Typically, portion 24 is rotated a number of times. As rotation continues cutting teeth 28 engage the central parts of cortical plates 15, 16 (FIG. 5), gradually removing cortical bone 14. At the end of the hollowing out of these plates, the cutting faces 26 of the central cutting portion 24 and the cutting teeth 28 have cut through the plates 15, 16 to form generally centrally located openings 19, 21. Remaining portions of plates 15, 16 then bear against the opposite faces 32 of non-cutting portion 31 and against non-cutting portion 36.

(e) Then, the surgeon withdraws tool 22 from between vertebrae V1, V2.

(f) Next, the surgeon inserts implant 1, previously filled with the bone graft G, between the plates 15, 16 from the rear to a suitable position by presenting the terminal part 6 and the bearing flanges 9 at the front end. The implant 1 is presented flat, so that longitudinal walls 4 are generally parallel to the cortical plates 15, 16 and initially come into contact therewith during insertion.

(g) Thereafter, the surgeon turns implant 1 through a quarter of a turn about its longitudinal axis (YY) so as to place it in the position shown in FIG. 6 with walls 4 substantially perpendicular to the cortical plates and its flat surfaces 12, 13 generally parallel to ,cortical plates 15, 16. Implant 1 may be inserted and turned by engaging hole 1 1a with a correspondingly threaded shaft of an accessory tool (not shown). The edges 4a of the longitudinal walls 4 which define projections 3a, 3b are inserted into openings 19, 21 thereby passing through plates 15, 16, while remaining portions of plates 15, 16 bear against flat surfaces 12, 13. Implant 1 is then in its final position in which it is stabilized. The bone graft G is in contact with the spongy part S1, S2, promoting bone fusion.

(h) The surgeon removes the second distractor 41 then repeats the preceding sequence of stages (a) through (g) to mount a second spinal cage implant 1 by placing it in a position generally parallel to the first cage implant 1 on the other side of the axis of the spinal column resulting in the configuration depicted in FIG. 7 (implants 1 are shown in phantom).

In other embodiments, it is envisioned that the described stages may be altered, deleted, combined, repeated, or resequenced as would occur to those skilled in the art. By way of nonlimiting example, the procedure according to the present invention may utilize one or more different tools to prepare the spine for fixation by the implant of the present invention. In another example, the tool of the present invention may be utilized to prepare a surgical site for a different implant.

Indeed, the scope of the invention is not intended to be limited to the described embodiment and may also include variants within the scope of the accompanying claims. For example, terminal bearing surfaces 12, 13 for the vertebral plates may have any shape, such as a curved or cylindrical shape with plates 15, 16 being correspondingly cut so as to allow placing the bearing surfaces in a suitable position. Further, these bearing surfaces may be interconnected in pairs and constitute a single member 50 as shown in FIG. 6.

Likewise, the central part of the implant of the present invention may have any shape, preferably retaining edges that project from the terminal bearing parts. In particular, the body may have a multitude of cells. Also, it should be generally noted that the implant and tool of the present invention may be adapted to a geometry of the spine with respect to lordosis, cyphosis or parallel vertebral end plates. Thus, the present invention includes application to adjacent vertebrae other than L3, L4. Correspondingly, the implant and the cutting portion of the tool may have a different shape, such as a cylindrical geometry other than the generally conical geometry depicted. Also, Instead of using the disclosed implant 1, the spinal space prepared by tool 22 can be filled with any other material as would occur to those skilled in the art.

According to other embodiments, the implant can be partly or totally constituted by porous rehabitable or resorbable materials favoring osteointegration. Such embodiments include: (a) an implant according to the above-illustrated geometry entirely made of a resorbable or rehabitable material; (b) an implant in which the whole of the central part is made of a resorbable or rehabitable material; or (c) an implant in which the periphery of the central part is made of a metallic or other material and the inside part is of a material favoring osteointegration that may be in an initially solid, pasty or liquid state.

In another alternative embodiment an implant is provided with only one bearing end part in which the end portion opposite to the bearing end part is open and forms a U shape for receiving a bone graft or a rehabitable or resorbable material.

French Patent Application Number 97 10664 filed on Aug. 26, 1997 to which priority is claimed is hereby incorporated by reference as if it were specifically set forth in its entirety herein. While the invention has been illustrated and described in detail in the drawings and foregoing description, the same is to be considered as illustrative and not restrictive in character, it being understood that only the preferred embodiments have been shown and described and that all changes, modifications, and equivalents that come within the spirit of the invention as defined by the following claims are desired to be protected.

What is claimed is:

1. An implant for insertion between a first vertebra and a second vertebra, the first vertebra having a first cortical bone plate and the second vertebra having a second cortical bone plate, characterized in that the implant comprises:

a first terminal part defining a first bearing surface to bear against the first cortical bone plate, a second bearing surface opposite said first surface to bear against the second cortical bone plate;

a second terminal part opposite said first terminal part, said second terminal part defining a third bearing surface to bear against the first cortical bone plate and a fourth bearing surface opposite said third surface to bear against the second cortical bone plate;

an elongated central part including a pair of longitudinal walls having a generally trapezoid configuration defining a cavity therebetween each of said walls projecting transversely from the first and second terminal parts and including a tapering edge adapted to penetrate the first and second cortical bone plates, and a projection extending transverse to said walls and positioned between said cavity and said first terminal part, said projection configured to correspondingly penetrate the first or second cortical bone plate when said first and third surfaces bear against the first cortical bone plate and said secondhand fourth surfaces bear against the second cortical bone plate.

2. The implant of claim 1 comprising a second projection opposite said projection, said second projection extending transverse to said walls and positioned between said cavity and said second terminal part, said projection configured to correspondingly penetrate the first or second cortical bone plate when said first and third surfaces bear against the first cortical bone plate and said second and fourth surfaces bear against the second cortical bone plate.

3. The implant of claim 1 wherein said first terminal part includes a first flange defining said first surface and a second flange defining said second surface; and said second terminal part includes a third flange defining said third surface and a fourth flange defining said fourth surface.

4. The implant of claim 1 wherein said first, second, third, and fourth surfaces are generally flat.

5. The implant of claim 2 wherein the first projection, the second projection and the tapering edges of the longitudinal walls define an opening into the cavity.

6. An implant for insertion between opposing endplates of adjacent vertebrae, said implant comprising:
   an elongate body defining a longitudinal axis and having a cavity therein; said body comprising:
   a first end including a first planar surface and an opposite second planar surface, said first and second planer surfaces configured to engage with the opposing endplates of the adjacent vertebrae;
   a second end including a third planar surface and an opposite fourth planar surface, said third and fourth planer surfaces configured to engage with the opposing endplates of the adjacent vertebrae;
   first and second longitudinal walls extending from the first end to the second end, each of said first and second walls having a first tapering edge and an opposite second tapering edge wherein the first and second edges are configured to penetrate the opposing endplates of the adjacent vertebrae;
   a first projection extending from the first planar surface in a direction generally transverse to the longitudinal axis, said first projection positioned adjacent the cavity, disposed between the first and second longitudinal walls, and configured to penetrate one of the adjacent vertebrae, and a third projection extending from the third planar surface in a direction generally transverse to the longitudinal axis, said third projection positioned adjacent the cavity, disposed between the first and second longitudinal walls and configured to penetrate one of the adjacent vertebrae.

7. The implant of claim 6 comprising:
   a second projection extending from the second planar surface in a direction generally transverse to the longitudinal axis and opposite said first projection; and,
   a fourth projection extending from the fourth planar surface in a direction generally transverse to the longitudinal axis and opposite said third projection.

8. The implant of claim 6 wherein the first tapering edges of the first and second longitudinal walls, the first projection, and the third projection define an opening into the cavity.

9. The implant of claim 6 wherein at least a portion of the implant is composed of a resorbable material.

10. The implant of claim 6 comprising a flange extending from the first end.

11. The implant of claim 10 comprising a flange extending from the second end.

12. The implant of claim 6 comprising a first opening and an opposite, second opening into the cavity to define a passageway through the implant in a direction traverse to the longitudinal axis.

13. The implant of claim 12 comprising a bone graft material in the cavity to contact spongy bone of the opposing vertebrae.

14. The implant of claim 1 wherein the tapering edge of each of the longitudinal walls extends in a longitudinal direction.

15. The implant of claim 1, wherein said walls each have a generally trapezoidal contour.

16. The implant of claim 1, wherein said cavity holds bone graft material.

17. The implant of claim 1, wherein at least a portion of the implant is composed of a porous material.

18. The implant of claim 1, wherein said first and second surfaces are separated by a first distance and said third and fourth surfaces are separated by a second distance greater than said first distance to accommodate a spinal curvature.

* * * * *